(12) United States Patent
Spiller et al.

(10) Patent No.: US 12,070,507 B2
(45) Date of Patent: Aug. 27, 2024

(54) COMPLEXES AND METHODS OF REDUCING INFLAMMATION

(71) Applicant: Drexel Univeristy, Philadelphia, PA (US)

(72) Inventors: Kara Lorraine Spiller, Glenside, PA (US); Amanda Elizabeth Pentecost, Blackwood, NJ (US); Yury Gogotsi, Ivyland, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 17/653,304

(22) Filed: Mar. 3, 2022

(65) Prior Publication Data

US 2022/0184226 A1 Jun. 16, 2022

Related U.S. Application Data

(60) Continuation of application No. 16/802,219, filed on Feb. 26, 2020, now abandoned, which is a division of
(Continued)

(51) Int. Cl.
*A61K 47/69* (2017.01)
*A61K 31/573* (2006.01)
(Continued)

(52) U.S. Cl.
CPC ........ *A61K 47/6923* (2017.08); *A61K 31/573* (2013.01); *A61K 47/52* (2017.08); *A61K 47/6929* (2017.08); *A61P 29/00* (2018.01)

(58) Field of Classification Search
CPC ... A61P 29/00; A61K 47/6929; A61K 31/573; A61K 47/6923; A61K 47/52
See application file for complete search history.

(56) References Cited

U.S. PATENT DOCUMENTS 6,187,822 B1 2/2001 Leibovich
9,186,190 B2 * 11/2015 Zhou ...................... A61P 29/00
(Continued)

FOREIGN PATENT DOCUMENTS

WO 2006007846 A2 1/2006
WO 2015028901 A1 3/2015

OTHER PUBLICATIONS

1-Octadecene: https://pubchem.ncbi.nlm.nih.gov/compound/1-Octadecene (Year: 2023).*
(Continued)

*Primary Examiner* — Hong Yu
(74) *Attorney, Agent, or Firm* — Saul Ewing LLP; Kathryn Doyle; Justin Crotty

(57) ABSTRACT

One aspect of the invention provides a method for reducing inflammation in a patient including locally administering a composition comprising a complex comprising octadecylamine surface-functionalized nanodiamonds with dexamethasone bound to octadecylamine. Another aspect of the invention provides a method for reducing inflammation in a patient comprising locally administering a composition including octadecylamine surface-functionalized nanodiamonds, wherein no therapeutic agent is bound to the nanodiamonds.

8 Claims, 10 Drawing Sheets

Related U.S. Application Data application No. 15/945,903, filed on Apr. 5, 2018, now abandoned.

(60) Provisional application No. 62/482,041, filed on Apr. 5, 2017.

(51) Int. Cl.
*A61K 47/52* (2017.01)
*A61P 29/00* (2006.01)

(56) References Cited

U.S. PATENT DOCUMENTS

| | | | |
|---|---|---|---|
| 2007/0184121 A1* | 8/2007 | Sung | A61Q 5/02 424/499 |
| 2010/0092577 A1* | 4/2010 | Guasti | A61K 9/0034 424/618 |
| 2010/0305309 A1 | 12/2010 | Ho et al. | |
| 2011/0006218 A1 | 1/2011 | Mochalin et al. | |
| 2012/0271361 A1* | 10/2012 | Zhou | A61B 17/866 514/769 |
| 2015/0096935 A1 | 4/2015 | Mitra et al. | |
| 2016/0279286 A1 | 9/2016 | Spiller et al. | |

OTHER PUBLICATIONS

1-Octadecene: https://datasheets.scbt.com/sc-255857.pdf. (Year: 2010).*
"Wikipedia, Dexamethasone", https://en.wikipedia.org/wiki/Dexamethasone, Mar. 23, 2017, 9 pages.
Zhang, Q. , "Mechanical properties and biomineralization of multifunctional nanodiamond-PLLA composites for bone tissue engineering", Biomaterials 33, 2012, 5067-5075.

* cited by examiner

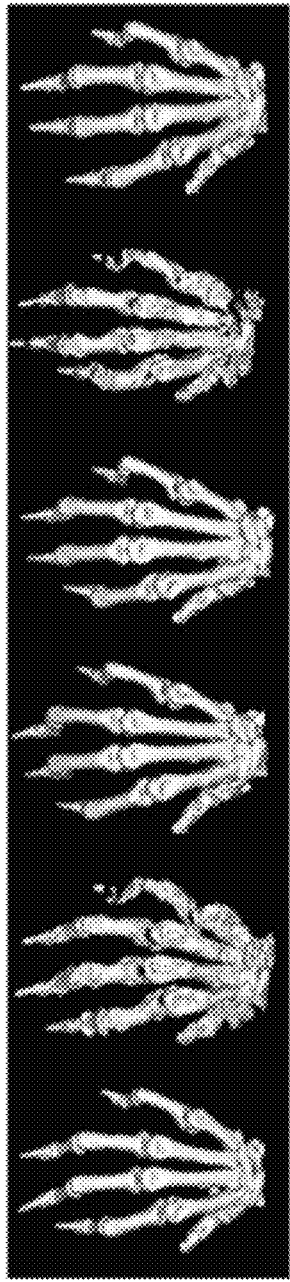
FIG. 8A
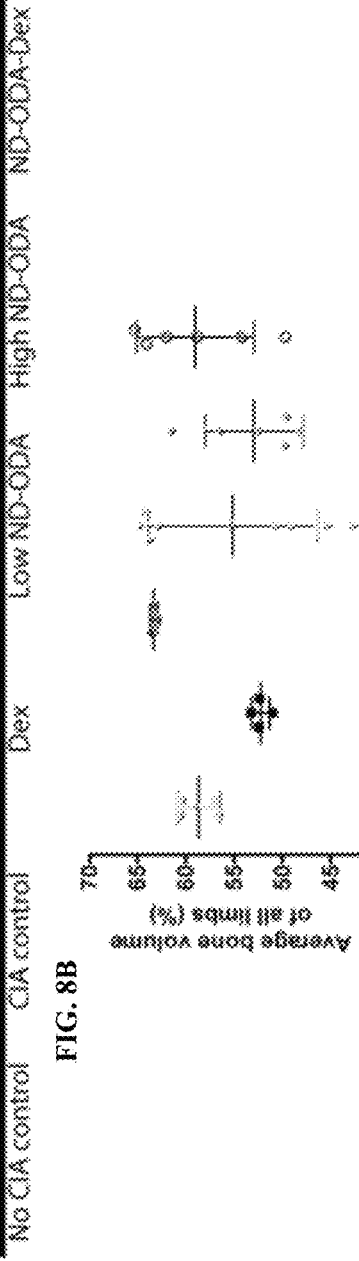
FIG. 8B
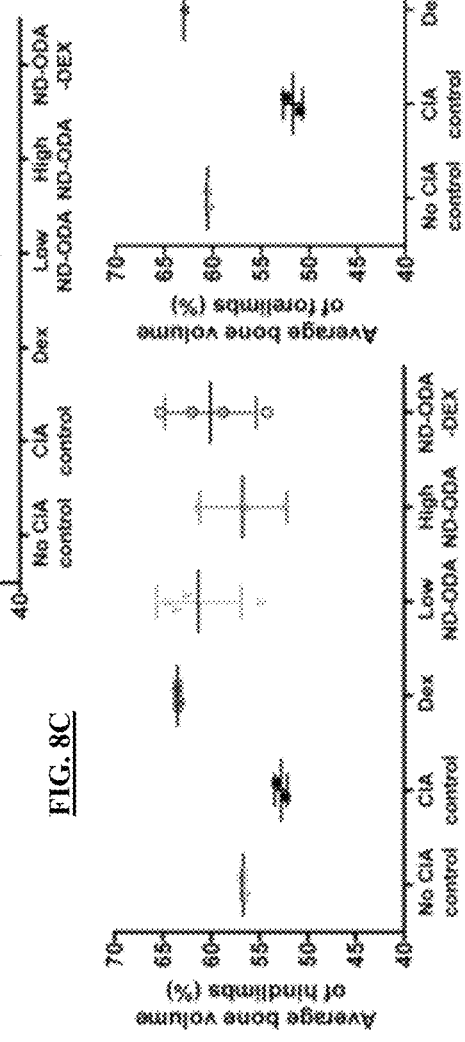
FIG. 8C
FIG. 8D

FIG. 9A CIA control (Score = 2)
FIG. 9B Dex (Score = 1.5)
FIG. 9C Low ND-ODA (Score = 1.5)
FIG. 9D High ND-ODA (Score = 3)
FIG. 9E ND-ODA-Dex (Score = 0.5)

CIA control (Score = 2)

Dex (Score = 1.5)

Low ND-ODA (Score = 1.5)

High ND-ODA (Score = 3)

ND-ODA-Dex (Score = 0.5)

COMPLEXES AND METHODS OF REDUCING INFLAMMATION

CROSS-REFERENCE TO RELATED APPLICATIONS

This application is a continuation under 35 U.S.C. § 120 of U.S. patent application Ser. No. 16/802,219, filed Feb. 26, 2020, which is a divisional under 35 U.S.C. § 120 of U.S. patent application Ser. No. 15/945,903, filed Apr. 5, 2018, which claims the benefit of priority under 35 U.S.C. § 119(e) to U.S. Provisional Patent Application Ser. No. 62/482,041, filed Apr. 5, 2017. The entire content of each application is hereby incorporated by reference herein.

STATEMENT REGARDING FEDERALLY SPONSORED RESEARCH OR DEVELOPMENT

This invention was made with government support under grant number NHLBI R01 HL130037 awarded by the National Institutes of Health, National Heart, Lung and Blood Institutes. The government has certain rights in the invention.

BACKGROUND OF THE INVENTION

Macrophages are innate immune cells that exhibit a broad range of behaviors, allowing them to act as key players in all aspects of the immune response, including tissue repair and disease. For example, in the normal healing response to an injury, pro-inflammatory M1 macrophages stimulate the inflammatory cascade, which signals the start of the healing process. A few days post-injury, M1 macrophages switch to the pro-healing/anti-inflammatory M2 phenotype. The M2 phenotype can be further divided into two major subgroups, each playing a distinct role in tissue repair: M2a macrophages, which are involved in tissue synthesis and maturation, and M2c macrophages, which are involved in the phagocytosis and clearance of apoptotic cells. The M2c phenotype is also believed to be involved in tissue remodeling and angiogenesis at early stages of wound healing. While it is now understood that macrophages exist in vivo on a spectrum of diverse phenotypes, including hybrid phenotypes, biomaterials that can modulate macrophage phenotype toward a particular set of behaviors would be highly beneficial for orchestrating tissue repair through the body's natural healing mechanisms.

SUMMARY OF THE INVENTION

In one aspect, the invention provides a complex including octadecylamine surface-functionalized nanodiamonds and dexamethasone. The dexamethasone is bound to the octadecylamine surface-functionalized nanodiamonds.

In various embodiments, the dexamethasone forms a monolayer on the octadecylamine surface-functionalized nanodiamonds.

In various embodiments, the complex has a particle size of less than about 7 µm.

In various embodiments, the complex has a particle size of about 1-2 µm and/or a particle size of about 150 nm.

Another aspect of the invention provides a method of reducing inflammation in a patient. The method includes administering the complex as described herein.

In various embodiments, the site of inflammation is a lesion or diabetic ulcer.

In various embodiments, the inflammation is caused by rheumatoid arthritis, Crohn's disease, asthma, inflammatory bowel disease, venous leg ulcers, diabetes, psoriasis or multiple sclerosis.

In various embodiments, the complex is delivered to the skin, the intestine, the lungs, trachea, or kidney of the subject.

In various embodiments, the patient's macrophages phagocytose the octadecylamine surface-functionalized nanodiamonds.

In various embodiments, the complex is locally administered.

In another aspect, the invention provides method of reducing inflammation in a patient. The method includes administering a composition comprising octadecylene surface-functionalized nanodiamonds. The surface functionalized nanodiamonds do not bind a substantial amount of a therapeutic agent.

In various embodiments, the site of inflammation is a lesion or diabetic ulcer.

In various embodiments, the inflammation is caused by rheumatoid arthritis, Crohn's disease, asthma, inflammatory bowel disease, venous leg ulcers, diabetes, psoriasis or multiple sclerosis.

In various embodiments, the composition is delivered to the skin, the intestine, the lungs, trachea, or kidney of the subject.

In various embodiments, the patient's macrophages phagocytose the surface-functionalized nanodiamonds.

In various embodiments, the surface-functionalized nanodiamonds have a particle size of less than about 7 µm.

In various embodiments, the surface-functionalized nanodiamonds have a particle size of about 1 µm.

In various embodiments, the surface-functionalized nanodiamonds are locally administered.

In another aspect, the invention provides a method of reducing a level of M2A macrophages in a patient. The method includes administering a composition including octadecylene surface-functionalized nanodiamonds. The surface functionalized nanodiamonds do not bind a substantial amount of a therapeutic agent.

In various embodiments, the nanodiamonds are aggregated, unaggregated or partially aggregated.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 1, Panel B is a schematic depicting an overview of methods of macrophage polarization. Peripheral blood monocytes were differentiated into M0 macrophages. At day 5, the cells were either kept as M0 or further polarized into M1 and M2a phenotypes in ultra-low attachment well-plates. FIG. 1, Panel C is a schematic depicting the effects of DEX, ND-ODA and ND-ODA-DEX complexes on polarized macrophages. After polarization was complete at day 7, either Dex, ND-ODA (at low, medium, or high concentrations), or Dex-loaded (ND-ODA-Dex; at low Dex and low ND concentrations) was added to cells and incubated for 6 h prior to RNA isolation and gene expression analysis.

FIG. 2, Panel B is a graph depicting the adsorption isotherm of DEX onto ND-ODA fit to Langmuir and Freundlich isotherm models. FIG. 2, Panel C depicts FTIR spectra showing the successful carboxylation of ND (ND-COOH), ODA attachment to ND (ND-ODA), and adsorption of Dex onto ND-ODA (ND-ODA-Dex). FIG. 2, Panel D is a graph depicting the particle size distribution of ND-ODA and ND-ODA-DEX after being bath sonicated for 1 min, and filtered using a 10 μm cell strainer.

FIG. 8A depicts representative reconstructed images from microCT. Images displayed are from non-CIA and untreated CIA control forelimbs, as well as forelimbs treated with Dex, low ND-ODA, high ND-ODA, and ND-ODA-Dex.

FIG. 8B depicts analysis of the average bone volume for all limbs per mouse (N=3-9).

FIG. 8C depicts analysis of the average bone volume of the hindlimbs (N=2-4).

FIG. 8D depicts analysis of the average bone volume of the forelimbs (N=1-5).

FIGS. 9A-E depicts hematoxylin and eosin staining for hindlimbs of CIA mice that were untreated (FIG. 9A), or treated with Dex (FIG. 9B), low ND-ODA (FIG. 9C), high ND-ODA (FIG. 9D) or ND-ODA-Dex. The arthritic scores associated with each presented hindlimb tissue section are also displayed. All scale bars are 250 μm.

DETAILED DESCRIPTION

Definitions

Figure 1:
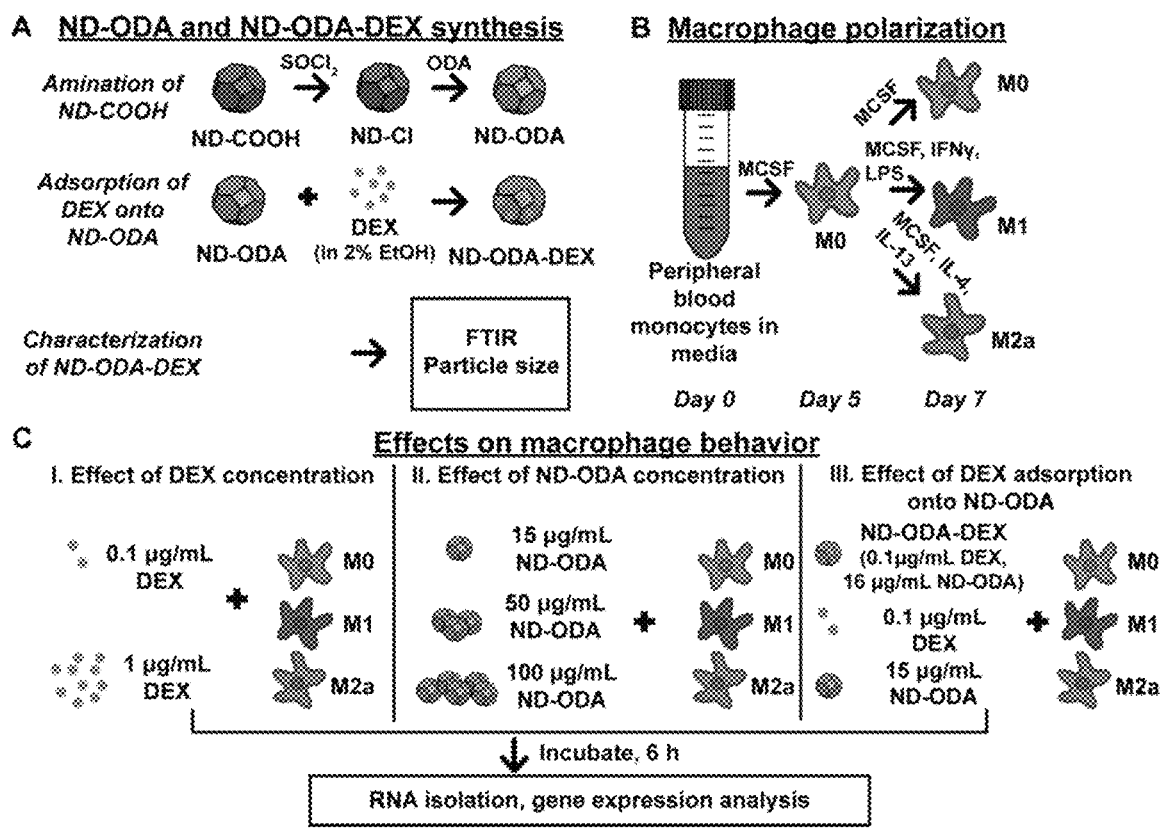
FIG. 1, Panel A is a schematic depicting an overview of the synthesis of nanodiamond octadecylamine (ND-ODA) dexamethasone (DEX) complexes. ND-ODA was synthesized by aminating ND-ODA. Then, DEX was adsorbed onto ND-ODA.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "binding" or "bound" refer to the adherence of molecules to one another by weak intermolecular forces such as hydrogen bonding or hydrophobic interaction, such as, but not limited to, enzymes to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

An "effective amount" or "therapeutically effective amount" of a compound is that amount of compound sufficient to provide a beneficial effect to the subject to which the compound is administered. An "effective amount" of a delivery vehicle is that amount sufficient to effectively bind or deliver a compound.

As used herein, "local administration" as used herein means direct application of a composition to the site of injury or pathology. No specific means of administration is implied.

The term "nanodiamond" as used herein means diamond particles with the structure of cubic or hexagonal diamond and particle (crystal) size between 1 and 100 nm (typically, around 5 nm). We use the term "detonation nanodiamond" to describe diamond nanoparticles with the size 2-10 nm produced by detonating explosives in a closed chamber.

The term "particle size" as used herein refers to the diameter of a nanoparticle as measured by any suitable technique. A non-limiting example of a method for measuring particle size is dynamic light scattering. The term may be applied to aggregates of particles or may be applied to isolated particles.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

A "therapeutic" treatment is a treatment administered to a subject who exhibits signs of pathology, for the purpose of diminishing or eliminating those signs.

As used herein, the term "therapeutically effective amount" is an amount of a compound of the invention, that when administered to a patient, ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, "treating a disease or disorder" means reducing the frequency with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Chronic inflammatory conditions, such as rheumatoid arthritis and chronic diabetic ulcers, are associated with an impaired transition from the M1 to the M2a phenotype. These stalled M1 macrophages overproduce inflammatory cytokines, leading to the destruction of surrounding tissues, and, consequently, chronic pain. Therefore, strategies that inhibit M1 polarization can be used to treat chronic inflammation. Moreover, biomaterials that promote M2 phenotypes (including M2a, M2c, etc.) may promote specific aspects of tissue repair through the actions of host macrophages. Conversely, an extended presence of M2a macrophages can also be detrimental. As part of the foreign body response to an implanted biomaterial, macrophages exhibiting characteristics of both M1 and M2a phenotypes can fuse together to form multinucleated giant cells that promote fibrous capsule formation around the implant. As a result, the implant is isolated from the rest of the body, thus leading to a lack of biointegration and ultimately failure. Therefore, it is essential to strategically engineer biomaterials to restore a balance in macrophage behavior.

Delivery of glucocorticoids like dexamethasone (Dex) has been employed to reduce both M1-mediated inflammation and fibrous capsule formation as well as enhance phagocytosis of apoptotic cells and bacteria. However, glucocorticoid receptors are found in the cytoplasm of nearly all cells. Consequently, glucocorticoids react with many different cell types and produce many off-target effects, including decreased drug accumulation at the affected site and broad suppression of the adaptive immune system by inducing lymphocyte apoptosis. Therefore, there is a need to develop a targeted drug delivery system that specifically delivers Dex to macrophages in order to effectively increase drug potency and reduce off-target effects.

Detonation nanodiamond (ND) is a commercially-available carbon nanomaterial that has attracted much attention from the biomedical field because of its many unique material properties, including its small primary particle size (~5 nm), rich surface chemistry, cytocompatibility with various cell lines, and ability to function as a platform for the delivery of drugs with diverse chemistries.

Without being bound by theory, Applicant believes that octadecylamine surface-functionalized nanodiamonds (ND-ODA) have standalone immunomodulatory properties, including inhibiting inflammation and promoting phagocytosis, ND-ODA is an unexpectedly effective delivery vehicle for dexamethasone, and ND-ODA-DEX complexes may provide a combination therapy in which anti-inflammatory effects are provided both by the release of dexamethasone from the complexes and residual ND-ODA.

Octadecylamine Surface-Functionalized Nanodiamond-Dexamethasone Complexes

Figure 2:
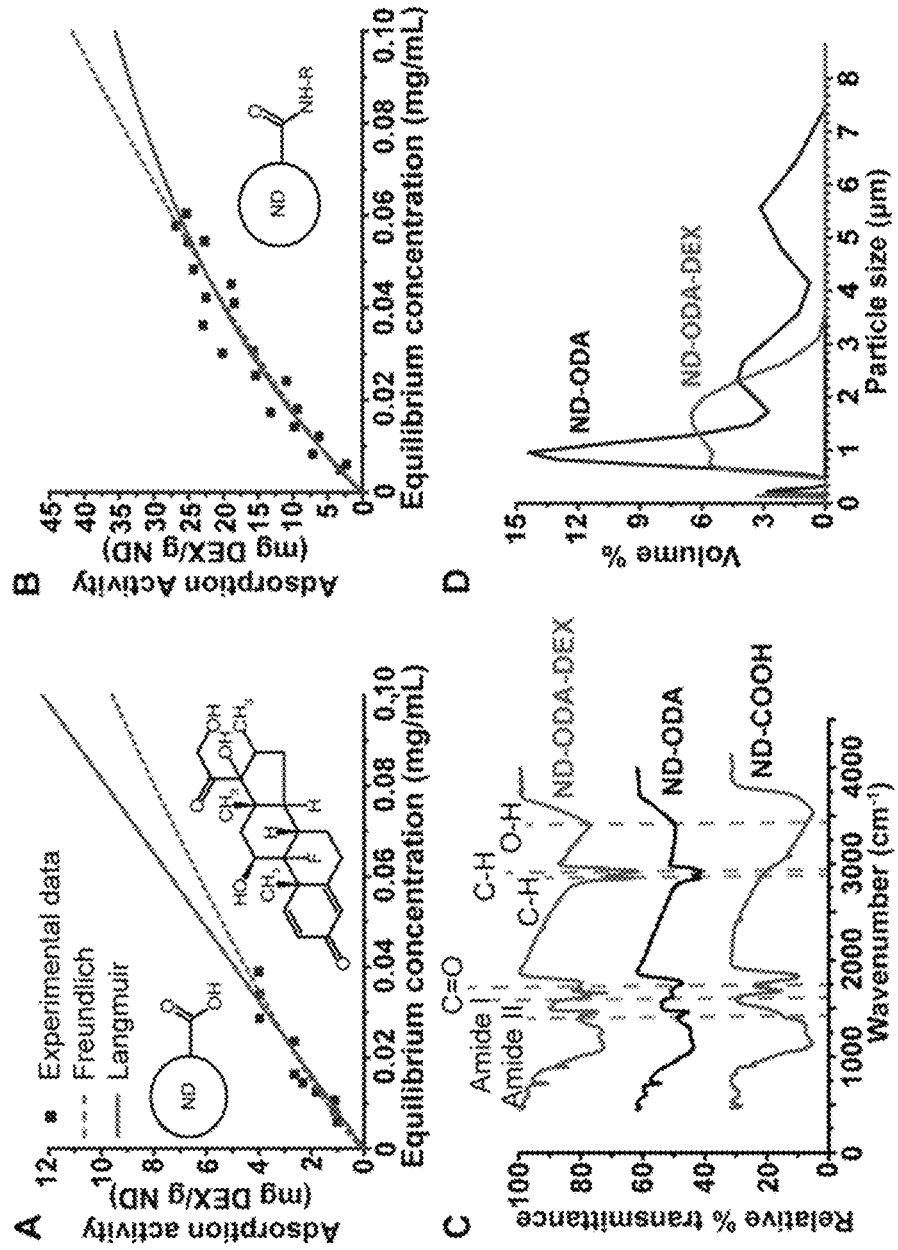
FIG. 2, Panel A is a graph depicting the adsorption isotherm of DEX onto ND-COOH fit to Langmuir and Freundlich isotherm models.

In one aspect, the invention provides complexes comprising octadecylamine surface-functionalized nanodiamonds and dexamethasone, wherein dexamethasone is bound to octadecylamine. Non-limiting examples of methods for the synthesis of the surface-functionalized nanodiamond complexes are described in the method section of the examples. As shown in FIG. 2, the attachment of ODA onto the surface of NDs enhanced the adsorbtion of dexamethasone relative to ND-COOH. ND-ODA, a relatively newly described form of ND, was selected as the optimal platform for the delivery of Dex because of its relatively strong binding capacity and higher monolayer adsorption capacity in Dex's solubility range, compared to ND-COOH. Without wishing to be limited by theory, ND-ODA's superior adsorption properties could be due to the fact that Dex and ND-ODA are both hydrophobic and may preferentially bond to each other over water molecules.

In some embodiments the NDs are detonation NDs. In some embodiments, the NDs have a cross-sectional diameter less than one micron. Although NDs of any size may be employed without departing from the spirit of the invention, various embodiments may employ populations of nanodiamonds with different distributions of particle size. Fine tuning the size and size distribution of the nanodiamonds may, in certain embodiments, allow more efficient delivery of dexamethasone to various tissue types or lesions. In some embodiments, altering the particle size may also allow the fine tuning of the characteristics of dexamethasone release or altering the uptake pathways by which the NDs may enter macrophages and furthermore will have other advantages that will be recognized by persons of skill in the art. In some embodiments, the NDs have an average particle size of less than about 7 μm in diameter. In some embodiments, the nanodiamonds have an average paticle size of about 1-2 μm. In some embodiments, the NDs have a bimodal distribution of particle size. In some embodiments, the bimodal distribution includes a population of nanodiamonds with an average particle size of 1-2 μm and a second population of nanodiamonds with an average particle size of about 150 nm. In various embodiments the nanodiamonds may be aggregated, unaggregated or partially aggregated.

Figure 3:
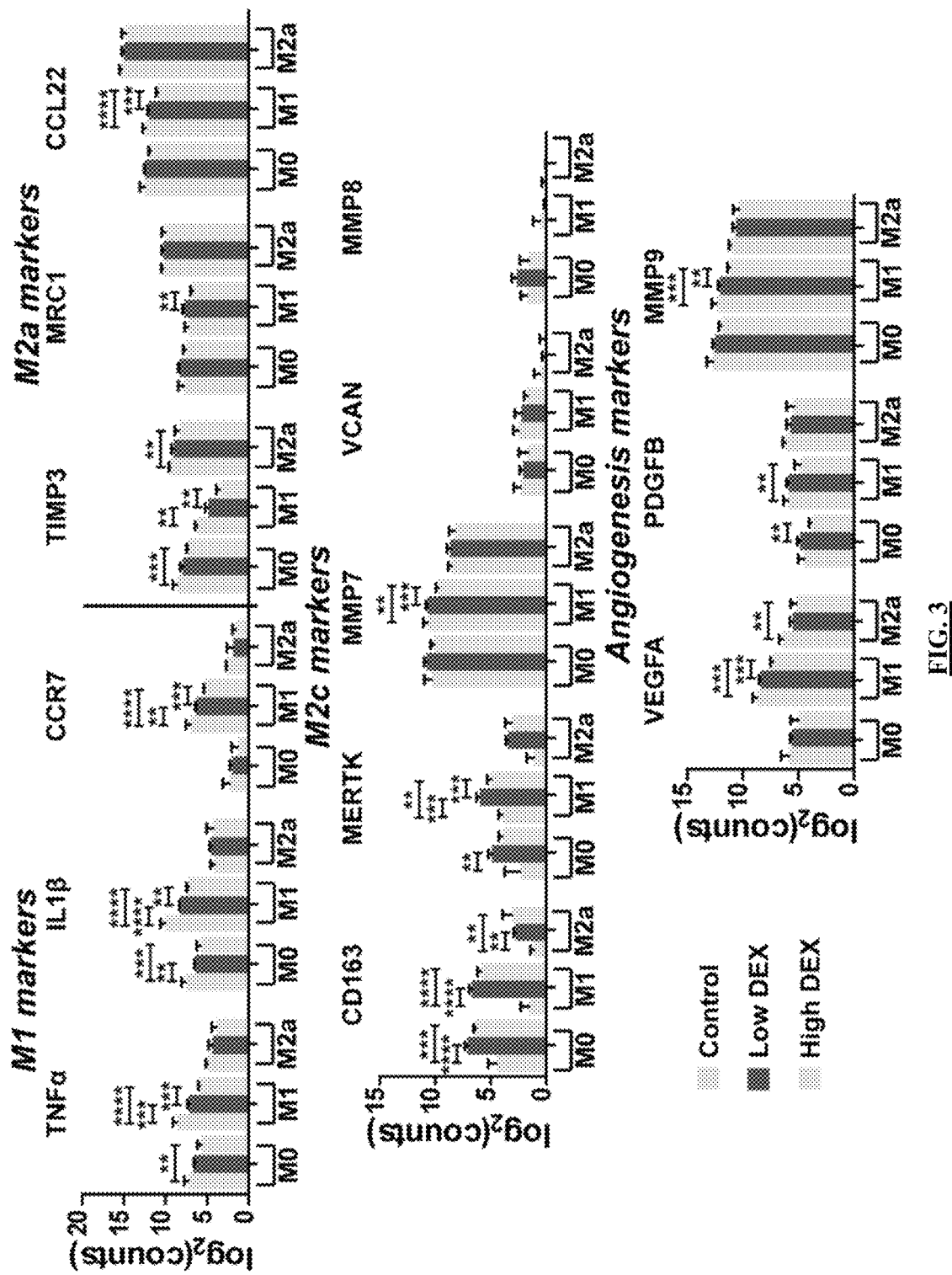
FIG. 3 is a graph depicting the effects of DEX on macrophage gene expression. Gene expression of proteins associated with M1, M2a, and M2c macrophages and angiogenesis were analyzed. Data are presented as Mean±SD. n=3-4 from a single donor. $p<0.01$, $*p<0.001$, $****p<0.0001$.
Figure 5:
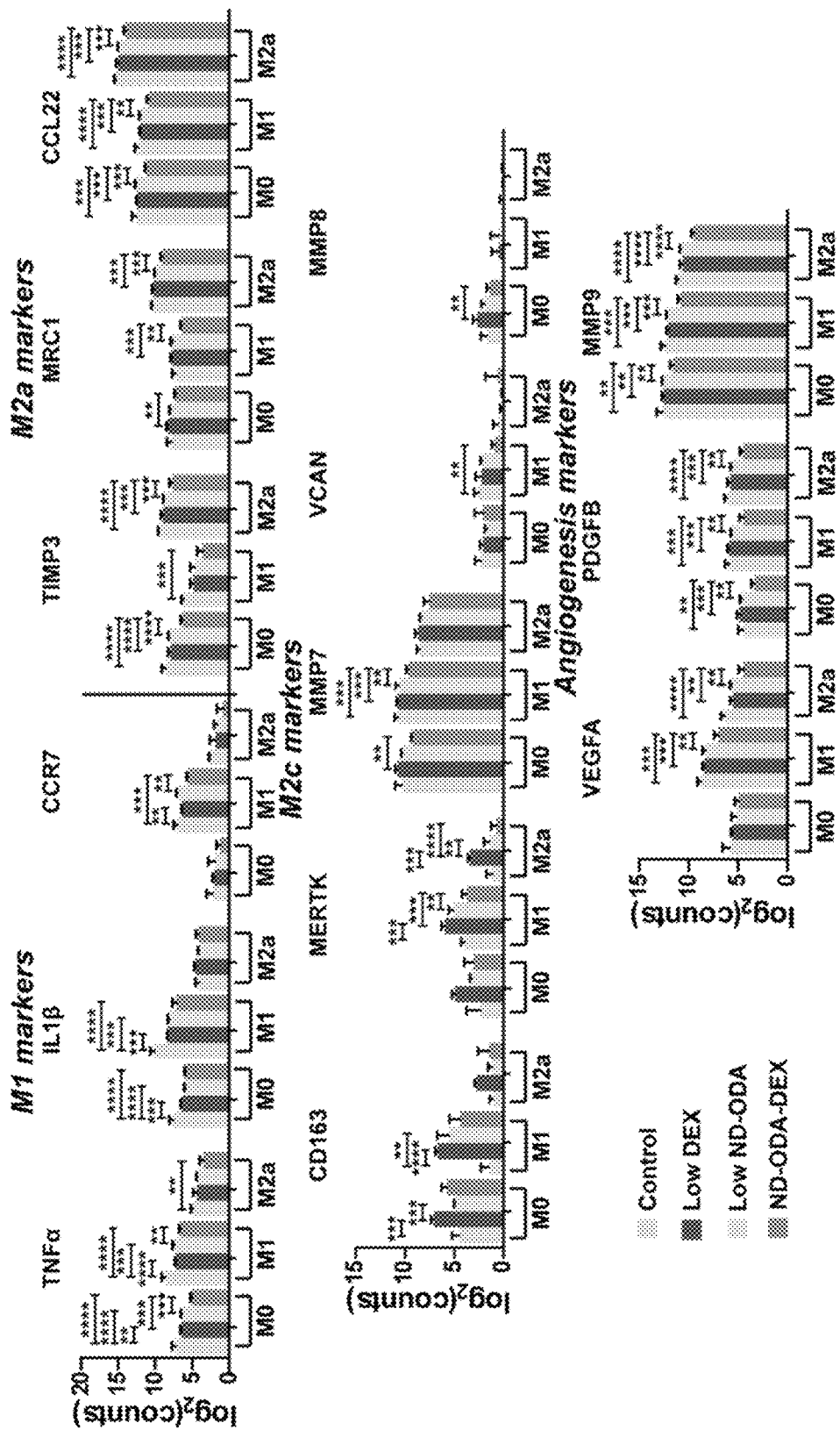
FIG. 5 is graph depicting the effects of ND-ODA-DEX on macrophage gene expression. Gene expression of proteins associated with M1, M2a, and M2c macrophages and angiogenesis were analyzed. Data are presented as Mean±SD. n=3-4 from a single donor. $p<0.01$, $*p<0.001$, $****p<0.0001$.

Method of Reducing Inflammation by Administering Octadecylamine Surface-Functionalized Nanodiamond-Dexamethasone Complexes In another aspect, the invention provides a method of reducing inflammation in a patient, by administering a complex including octadecylamine surface-functionalized NDs, and dexamethasone, wherein dexamethasone is bound to octadecylamine-functionalized ND. Without wishing to be limited by theory, macrophages present at the site of inflammation may phagocytose the nanodiamond-dexamethasoneND complexes and allow targeted delivery of dexamethasone thereby avoiding some off-target effects that may accompany other methods of delivering dexamethasone. The anti-inflammatory effects of ND-ODA-DEX on macrophage gene expression are shown in FIG. 5 and Example 6 and may be compared with the effects of Dex alone as shown in FIG. 3 and Example 4.

Without wishing to be limited by theory, ND may be able to escape the endosome and to situate itself in the cytoplasm for an extended period of time. Thus, ND potentially avoids lysosomal degradation, which would theoretically limit degradation of any loaded drugs. Moreover, because the glucocorticoid receptor is intracellular, escaping into the cytoplasm would allow for ND-glucocorticoid complexes to directly interact with intracellular receptors, rather than depending solely on the drug's diffusion through the endosome.

Those of skill in the art will understand that the method may be applied to a variety of sites of inflammation. In various embodiments, the method may be applied to any tissue affected by excessive inflammation. In some embodiments, the site of inflammation may be a lesion or diabetic ulcer. The method may also be applied to a variety of tissue types. In some embodiments the composition is delivered to the skin, the intestine, lungs, trachea, liver or the kidneys of the subject. The method may also be applied to inflammation associated with a variety of pathologies. In various embodiments the inflammation is caused by rheumatoid arthritis, Crohn's disease, asthma, inflammatory bowel disease, venous leg ulcers, diabetic ulcers, psoriasis, multiple sclerosis, and other inflammatory diseases. In some embodiments the composition is locally administered to a site of inflammation.

Figure 4:
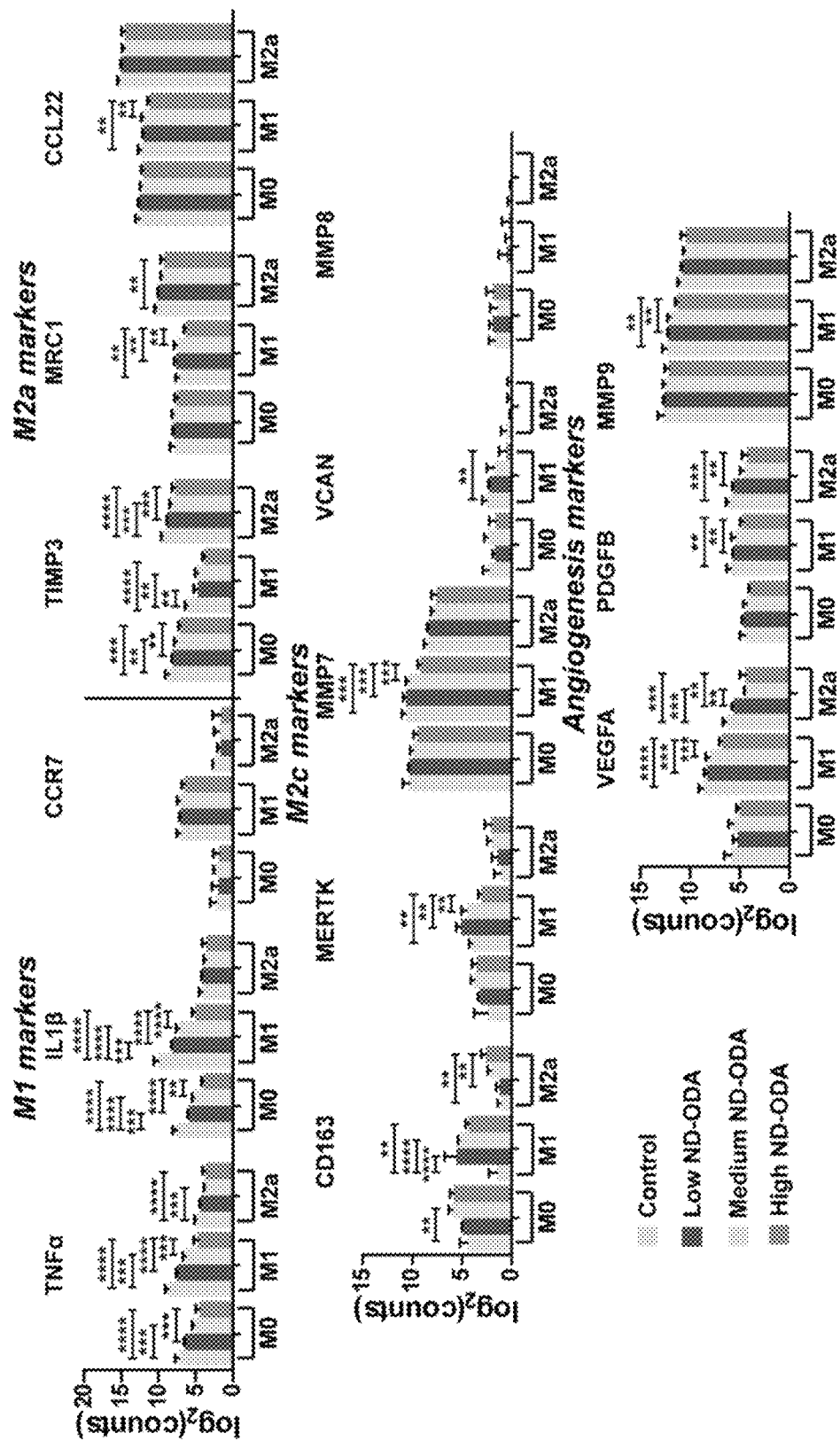
FIG. 4 is graph depicting the effects of ND-ODA on macrophage gene expression. Gene expression of proteins associated with M1, M2a, and M2c macrophages and angiogenesis were analyzed. Data are presented as Mean±SD. n=3-4 from a single donor. $p<0.01$, $*p<0.001$, $****p<0.0001$.

Method of Reducing Inflammation by Administering Octadecylamine Surface-Functionalized Nanodiamonds In a further aspect, the invention comprises a method of reducing inflammation in a patient, comprising locally administering a composition comprising octadecylene surface-functionalized nanodiamonds, wherein the nanodiamonds do not carry a substantial amount of a therapeutic agent. It has been unexpectedly discovered that ND-ODA has significant anti-inflammatory properties even in the absence of dexamethasone or any other therapeutic agent. The anti-inflammatory effects of ND-ODA on macrophage gene expression are shown in FIG. 4 and Example 5.

Without wishing to be bound by theory, it is possible that ND-ODA's anti-inflammatory behaviour may be due to (1) its recognition as apoptotic cells or cell debris, thus mimicking the process of efferocytosis; or (2) adsorption of haemoglobin, which triggers activation of macrophage CD163 receptors, thus leading to increased secretion of the anti-inflammatory cytokine IL-10. One of macrophages' key roles in wound resolution includes clearing apoptotic cells from the body, in a process called efferocytosis. During this process, macrophages phagocytose and remove the cells and switch to a phenotype characterized by secretion of anti-inflammatory cytokines such as IL-10 and TGF-β. Therefore, impaired clearance of apoptotic cells leads to increased pro-inflammatory cytokine levels, and, consequently, chronic inflammation. In various embodiments, the ND-ODA aggregates are micron-sized, ranging from to 1 to 7 μm, which falls directly in the size range of human cells of 1-10 μm. In addition, apoptotic cells display phosphatidylserine (PS), which acts as a signal for phagocytosis by macrophages. While the surface of ND-ODA does not completely mimic the structure of PS, a phospholipid with a hydrophobic fatty acid tail, it does display long hydrocarbon chains on its surface. It is also possible that haemoglobin adsorbed to the ND-ODA and triggered uptake through the CD163 receptor, which has a strong affinity for haemoglobin-haptoglobin complexes in the blood as well as haemoglobin. As a result of increased CD163 expression, IL-10 production may have also been increased, resulting in the suppression of pro-inflammatory genes, such as TNF and IL1B.

Although NDs of any size may be employed without departing from the spirit of the invention, various embodiments may employ populations of nanodiamonds with different distributions of particle size. In various embodiments the average particle size may be between about 1 and about 10 μm in diameter. In some embodiments, the average particle size is less than about 7 μm. In some embodiments the average particle size is about 1 μM. In some embodiments the distribution of particle sizes is bimodal. In further embodiments the distribution of particle sizes comprises a population with an average particle size around 1 μm and a second population with an average particle size around 150 nm.

Those of skill in the art will understand that the method may be applied to a variety of sites of inflammation. In various embodiments, the method may be applied to any tissue affected by excessive inflammation. In some embodiments, the site of inflammation may be a lesion or diabetic ulcer. The method may also be applied to a variety of tissue types. In some embodiments the composition is delivered to the skin, the intestine, lungs, trachea, liver or the kidneys of the subject. The method may also be applied to inflammation associated with a variety of pathologies. In various embodiments the inflammation is caused by rheumatoid arthritis, Crohn's disease, asthma or inflammatory bowel disease, venous leg ulcers, diabetic ulcers, psoriasis, multiple sclerosis, and other inflammatory diseases. In another aspect, the invention comprises a method of reducing a level of M2a macrophages in a patient comprising administering a composition comprising octadecylene surface-functionalized nanodiamonds, wherein the surface functionalized nanodiamonds do not bind a substantial amount of a therapeutic agent.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. In certain embodiments, the invention envisions administration of a dose which results in a concentration of the compound of the present invention from 0.1 nM and 10 μM in a mammal. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-fibrotic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

In certain embodiments, the tablets of the invention comprise mannitol, dibasic calcium phosphate anhydrous, crospovidone, hypromellose and magnesium stearate, with a film-coat containing hypromellose, macrogol 400, red iron oxide, black iron oxide and titanium dioxide. In other embodiments, the tablets of the invention comprise about 50 or 125 mg of saracatinib expressed as free base.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in International Publication Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. The data obtained from cell culture assays and animal studies are optionally used in formulating a range of dosage for use in human. The dosage of such compounds lies preferably within a range of circulating concentrations that include the ED50 with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the preferred embodiments of the present invention, and are not to be construed as limiting in any way the remainder of the disclosure.

The materials and methods employed in the experiments disclosed herein are now described.

Experimental Design

FIG. 1 illustrates the overall experimental design of this study. First, two ND platforms, ND-COOH and ND-ODA, were synthesized and characterized for their Dex adsorption capacities (FIG. 1A). After confirming ND-ODA's adsorption properties, particle size and surface chemistry were analysed for the ND-ODA-Dex complexes.

Then, human monocytes, derived from peripheral blood, were differentiated into unactivated macrophages (M0) and either kept as M0, or polarized into M1 or M2a (FIG. 1B). Three studies were simultaneously performed to determine the effects of Dex and/or ND-ODA on macrophage gene expression (FIG. 1C). In the first study, the effect of DEX concentration was explored by separately adding low and high concentrations of Dex to M0, M1, and M2a macrophages. In the second study, the effect of ND-ODA concentration was similarly studied, using low, medium, and high concentrations of ND-ODA. Finally, in the third study, Dex-adsorbed ND-ODA was evaluated, using the low doses of both Dex and ND-ODA.

The expression levels of 14 genes indicative of macrophage phenotype and angiogenesis were analysed to determine changes in macrophage behaviour. TNF, IL1B, and CCR7 were selected as M1 markers. TIMP3, MRC1, and CCL22 were selected as M2a markers. Additionally, 5 M2c markers were used. CD163 and MERTK were selected because of their roles in phagocytosis. MMP7 and MMP8 were selected because of their roles in extracellular matrix remodelling. VCAN, which contributes to cell adhesion properties, was also selected as an M2c marker. Because of their roles in angiogenesis and tissue healing, VEGFA, PDGFB, and MMP9 were also investigated. Additionally, VEGFA can be classified as an M1 marker; PDGFB can be classified as an M2a marker.

Synthesis of ND-COOH and ND-ODA

As-received UD90 grade ND (donated by sp3 Diamond Technologies) was first air oxidized at 425° C. for 5 h and then acid purified by refluxing with an nitric acid/hydrochloric acid mixture at 90° C. for 24 h in order to simultaneously decrease the sp2-bonded carbon content and attach carboxyl (COOH) surface groups (ND-COOH). To produce octadecylamine-functionalized ND (ND-ODA), 1.5 g ND-COOH was reacted with thionyl chloride in presence of anhydrous N,N-dimethylformamide (DMF), which is well known as a catalyst for this reaction, at 70° C. for 24 h to produce ND-COCl. The highly reactive —Cl groups were then replaced with —NH$_2$ groups, connected to a long aliphatic chain, through reacting with 1 g octadecylamine at 90° C. for 96 h, and then rinsing with methanol to remove excess reactant.

Adsorption activity of DEX onto ND-COOH and ND-ODA

To characterize adsorption activity, 5 mL samples of increasing concentrations of dexamethasone (SIGMA-ALDRICH®, D4902), in 2% ethanol were used. Because of Dex's low solubility even with the addition of ethanol, the range of initial dexamethasone concentrations was between 5 and 120 µg/mL. ND-COOH or ND-ODA (2±0.1 mg) was added to solutions of varied Dex concentrations, and bath sonicated for ~1 min in order to break up large aggregates. Then, the samples were placed on an orbital shaker in the dark at room temperature, and were left to shake overnight at 200 rpm (THERMO FISHER® MAXQ™ 4450). The samples were then centrifuged at 4000 rpm (3220 g, Eppendorf 5810R) for 2 h. The supernatant, which consisted of unbound Dex, was collected for UV-visible spectrophotometry (UV-VIS) analysis (THERMO SCIENTIFIC® NANODROP® 1000, 243 nm), and the concentration was calculated from the measured absorbance using a calibration curve. The calculated concentrations of non-adsorbed drug in the supernatant, also known as the equilibrium concentrations, were subtracted from the initial concentrations to determine the mass of the drug adsorbed. Then, the adsorption activities for each sample were calculated by dividing the individual calculated masses of the drug (mg) adsorbed by the known masses of ND (g) that were used to adsorb the drug in each sample. To construct the adsorption isotherms, the experimental adsorption activities for each concentration of Dex were plotted for each corresponding equilibrium concentration. These data points were subjected to fitting using two common adsorption isotherm models, Langmuir and Freundlich, in order to determine the adsorption mechanism (mono- or multilayer, hetero- or homogeneous adsorption, etc.). The models differ with respect to their key assumptions and their mathematical representations. The Langmuir isotherm assumes monolayer adsorption with a distinct number of available adsorption sites, which are all equivalent and independent. It also assumes that the adsorbate (drug) is immobilized upon contact. Mathematically, Langmuir adsorption is represented as:

$$A = \frac{K_L A_{max} C_{eq}}{1 + K_L C_{eq}}$$

where A is the calculated adsorption activity for each equilibrium concentration ($C_{eq}$), while $A_{max}$ is the predicted maximum possible adsorption capacity for a single monolayer, and KL is a predicted value corresponding to the bond strength between the adsorbent and adsorbate. On the other hand, the empirical Freundlich isotherm assumes that adsorption can be either multi- or monolayer, and that the adsorption sites are heterogeneous. Mathematically, Freundlich adsorption is represented as:

$$\log(A) = \log(K) + n(\log(C_{eq}))$$

where K and n are arbitrary constants which do not provide any information about the adsorption capacity of a monolayer or its bond strength.

The experimental adsorption isotherm data were fit to both Langmuir and Freundlich models by means of nonlinear least-squares fitting using MICROSOFT® EXCEL® Data Solver. Using EXCEL® software, Pearson's correlation coefficient (R) was also calculated and used to determine goodness of fit.

Characterization of ND and ND-ODA-DEX

Because of its superior adsorption properties, further analysis was carried out on ND-ODA and maximally loaded (~25 mg Dex/g ND-ODA) Dex-adsorbed ND-ODA complexes (ND-ODA-Dex). FTIR (PERKINELMER® SPECTRUM ONE™) analysis was performed in ambient environment and spectra on ND-COOH, ND-ODA, and ND-ODA-Dex were recorded. All samples were freeze-dried, finely ground with potassium bromide (KBr) powder, and pressed into a pellet prior to FTIR analysis. Dynamic light scattering (DLS) was used to measure particle size (MALVERN® ZETASIZER® NANO ZS™). Prior to DLS analysis, ND-ODA and maximally-loaded ND-ODA-Dex were dispersed in PBS, bath sonicated for 1 min, and then filtered using a 10 µm cell strainer (PLURISELECT™) in order to remove aggregates that are too large for phagocytosis. The average particle size distribution was calculated from 5 repeated experiments.

Differentiation and Polarization of Primary Human Macrophages

Human monocytes derived from peripheral blood from a single donor were obtained from the Human Immunology Core at the University of Pennsylvania (Philadelphia, PA). The monocytes were differentiated into macrophages (M0) by culturing in ultra-low attachment flasks with RPMI 1640 media supplemented with 10% heat-inactivated human serum (from human male AB plasma, Sigma Aldrich), 1% penicillin/streptomycin, and 20 ng/mL macrophage colony stimulating factor (MCSF). On day 3, the media was refreshed. On day 5, the M0 macrophages were gently scraped, counted, and plated with fresh MCSF-supplemented media into 24 well plates at a concentration of 106 cells/mL. Polarization was then performed by adding 100 ng/mL interferon-gamma (IFNγ) and 100 ng/mL lipopolysaccharide (LPS) for M1 or 40 ng/mL interleukin-4 (IL4) and 20 ng/mL interleukin-13 (IL-13) for M2a 39. After 2 days of polarization, the media was replaced with cytokine-free media containing ND samples as described below.

Treatment of Macrophages with DEX, ND-ODA, and ND-ODA-DEX

To determine the effect of Dex on macrophages, a stock solution of 20 m/mL in cytokine-free media with 2% ethanol was prepared. Then, the concentrations were diluted in media to either 1 µg/mL (high Dex) or 0.1 µg/mL (low Dex), and added to the macrophages for 6 hr (n=4). To determine the effect of bare ND-ODA on macrophages, 330 µg/mL ND-ODA was dispersed in cytokine-free media, bath sonicated for 1 min, and filtered using a 10 µm cell strainer. In order to calculate the average mass loss after filtering ND-ODA and ND-ODA-Dex, the mass of the cell strainer was weighed before and after filtering, and the difference in mass was compared to the original mass of ND-ODA or ND-ODA-Dex. Because the average mass loss was calculated to be ~70%, the ND-ODA concentration was assumed to be ~100 µg/mL after filtering. This stock solution was either used directly (high ND-ODA) or diluted in cytokine-free media to produce concentrations of 50 µg/mL (medium ND-ODA) and 15 µg/mL (low ND-ODA). High, medium, and low concentrations of ND-ODA were added to the macrophages for 6 hr (n=3-4).

To determine the effect of ND-ODA-Dex on macrophages, ND-ODA-Dex samples were prepared to concentrations of low ND (15 µg/mL) and low Dex (0.1 µg/mL). Briefly, 4 mg ND-ODA was added to 10 µg/mL Dex in 2% ethanol, bath sonicated, and mixed overnight. Using UV-VIS as described above, the ND-ODA-Dex were determined to have an adsorption activity of ~6 mg Dex/g ND-ODA. Therefore, 1 mg of ND-ODA has approximately 6 µg Dex adsorbed to its surface. After separating the ND-ODA-Dex complexes by centrifugation and freeze-drying, 2 mg ND-ODA-Dex was rinsed once in PBS to ensure all unbound DEX had been removed. To make a dispersion with 0.1 µg/mL Dex, the 2 mg ND-ODA-Dex were dispersed in 37.5 mL, bath sonicated for 1 min, and filtered using a 10 µm cell strainer. With 70% mass loss, the final concentration of DEX was 0.1 µg/mL and the final concentration of ND-ODA was 16 µg/mL. This dispersion was then added to the macrophages (n=3-4). Cytokine-free media without ND-ODA was added to the controls (n=3). After incubating for 6 h, all macrophage samples were scraped and stored in TRIZOL® reagent (Invitrogen, USA) at −80° C. RNA was isolated from TRIZOL® reagent using chloroform followed by purification with the RNEASY® Micro Kit (QIAGEN®) according to the manufacturer's instructions.

NANOSTRING® Analysis

Expression of a custom-designed set of 20 genes (14 known markers of the M1, M2a, and M2c phenotypes as well as phagocytic and angiogenic genes plus 6 housekeeping genes) was analyzed using a NANOSTRING TECHNOLOGIES® NCOUNTER® Analysis System. Prior to analysis, AGILENT® RNA 6000 Nano Kits were used in combination with an AGILENT® 2100 bioanalyzer to determine RNA concentration. 100 ng RNA from each sample was diluted in 5 µL water and mixed with reporter/capture probe pairs for each gene, in addition to reporter/capture pairs for 8 negative and 6 positive controls, according to the manufacturer's instructions. The raw counts were normalized across the entire data set according to NanoString's NCOUNTER® Expression Data Analysis Guide. Briefly, the average geometric mean of the positive control counts was divided by the individual geometric means of the positive controls for each sample to determine sample-specific scaling factors. The data were then normalized by multiplying sample-specific scaling factors by the individual counts for each gene in each sample. The data were then log-transformed, and the average log-transformed negative control values for each lane were subtracted from each sample. Negative log-transformed gene expression values were regarded as zero. Statistical analysis was performed in GRAPHPAD™ PRISM™ software using a one-way ANOVA and Tukey's multiple comparisons test. P<0.01 was considered significant. Data are presented as mean±standard deviation (SD).

In Vivo Studies

Before evaluating the therapeutic efficacy of ND-ODA and ND-ODA-Dex in treating mice with collagen type II-induced arthritis (CIA), the method of administration needed to be established first. Because ND-ODA/ND-ODA-Dex aggregates are micron sized, it was possible that macrophages of the reticuloendothelial system (RES) would uptake ND-ODA/ND-ODA-Dex, resulting in their primary accumulation in the liver and spleen, and not the affected arthritic joints. Therefore, to visualize the biodistribution following systemic delivery in CIA mice, Cy5.5, a near-infrared dye, was conjugated to ND-ODA to produce ND-ODA-Cy5.5.

Dex was then adsorbed onto ND-ODA-Cy5.5, thus producing ND-ODA-Cy5.5-Dex. Aggregate sizes of both sets of complexed particles were analyzed following bath sonication and filtering in order to ensure that complexing with the dye did not significantly impact the micron size range. ND-ODA-Cy5.5 and ND-ODA-Cy5.5-Dex were systemically injected into CIA mice, and were monitored using in vivo real time imaging of the whole mice. After 24 h, the mice were sacrificed, and accumulation of the ND complexes in major organs as well as the arthritic limbs was determined.

The results from the biodistribution study informed the use of local delivery in future studies. The therapeutic efficacy of Dex, ND-ODA, and ND-ODA-Dex was then evaluated following two local injections, which were given 3 days apart. Arthritic forelimbs were injected at the wrists, whereas arthritic hindlimbs were injected at both the knees and the wrists. Over the course of 14 days following the first therapeutic injection, the paws were monitored and clinically scored according to the observed severity of inflammation. At the end of the study, the mice were sacrificed, and their arthritic limbs were excised.

Rheumatoid arthritis is characterized by the destruction of both bone and cartilage at joints, which is caused by resident and infiltrating synovial cells. M1 macrophages are among the most prominent types of infiltrating cells, as they secrete pro-inflammatory cytokines and chemokines, resulting in not only local destruction, but also the recruitment of more inflammatory cells to the affected joints. Therefore, to further characterize the therapeutic efficacy of ND-ODA and ND-ODA-Dex, compared to free Dex, bone degradation was assessed by using x-ray micro-tomography. Reconstructed 3D images of the diseased joints were generated and used to determined changes in bone volume. In order to assess changes on a cellular level, tissue sections of the joints were first analyzed using hematoxylin and eosin staining to determine changes in cell infiltration due to the presence of pro-inflammatory cells such as M1 macrophages. The relative levels of iNOS, a typical functional marker of M1 macrophages, at the arthritic joints was also visualized and analyzed using 3,3'-diaminobenzidine (DAB) staining. Taken together, these results represent a full analysis of the therapeutic effects of ND-ODA and ND-ODA-Dex on the physical symptoms, whole tissues, and cells that are affected by CIA in mice.

In order to visualize ND-ODA in real-time using near-infrared imaging, near-infrared (NIR) dye Cy5.5-NHS ester was conjugated to the surface of ND-ODA. Briefly, 10 mg ND-ODA was dispersed in 2 mL dimethylsulfoxide (DMSO). Then, 100 μL of 1 mg/mL Cy5.5-NHS in DMSO was added to the ND-ODA dispersion, and the mixture was bath sonicated in 30 min intervals until 2 h was reached. The samples were removed for 10 min in between intervals to prevent overheating. Next, the dispersion was centrifuged at ~28,000 g for 10 min, and rinsed with DI water until the supernatant was no longer blue. The resultant ND-ODA-Cy5.5 powder was freeze-dried. To confirm the successful attachment of Cy5.5-NHS, ND-ODA-Cy5.5 was dispersed in water and imaged using the NIR.

Dex was then adsorbed to ND-ODA-Cy5.5 to create ND-ODA-Cy5.5-Dex. Similarly to the procedure detailed above, 2 mg ND-ODA-Cy5.5 was added to 5 mL 100 μg/mL Dex in 2% ethanol, bath sonicated, and allowed to mix overnight. The ND-ODA-Cy5.5-Dex complexes were then centrifuged at 17,000 g, and the supernatant's absorbance was analyzed in UV-Vis at 265 nm, and compared against a Dex calibration curve to determine the mass of Dex adsorbed. Particle sizes of both ND-ODA-Cy5.5 and ND-ODA-Cy5.5-Dex in PBS were measured after bath sonication and filtering using a 10 μm cell strainer using a MALVERN® ZETASIZER® ZS.

To determine their therapeutic properties, ND-ODA and ND-ODA-Dex without Cy5.5 were used to treat collagen type II-induced (CIA) arthritic mice. 100 μg/mL ND-ODA was first prepared by dispersing 3.3 mg ND-ODA in 10 mL sterile PBS, and then filtered using a 10 μm cell strainer, assuming a 70% loss, as calculated previously. This stock solution was then diluted in PBS to 50 μg/mL ND-ODA (high ND-ODA) or 15 μg/mL ND-ODA (low ND-ODA). 0.1 μg/mL Dex was dispersed in sterile PBS. To match this Dex dose, as well as the low ND-ODA dose, ND-ODA-Dex was prepared by adsorbing 10 μg/mL Dex in 2% ethanol onto 4 mg ND-ODA. After mixing overnight, the ND-ODA-Dex complexes were centrifuged, and the supernatant was analyzed in UV-Vis at 265 nm to determine the amount of unadsorbed Dex. Then, the supernatant was disposed, and the sample was freeze-dried.

The volume of PBS needed to disperse 1 mg ND-ODA-Dex to produce a dispersion of 0.1 μg/mL Dex and 15 μg/mL ND-ODA was determined by using the calculated adsorption activity of ~6-9 mg Dex/g ND-ODA. This volume, which ranged 20-30 mL, accounted for the 30% mass loss (determined by averaging the weight of unfiltered ND-ODA-Dex) due to subsequent bath sonication and filtering of the dispersion through a 10 μm cell strainer.

Development of Collagen Type II-Induced Arthritic Mouse Model

Collagen type II-induced arthritis (CIA) was developed in male DBA/1J mice of 4 weeks in age using bovine type II collagen and complete and incomplete Freund's adjuvants according to the protocol (CHONDREX). To summarize, equal parts of bovine type II collagen and complete Freund's Adjuvant were mixed and cooled on ice. 100 μL of the emulsion was injected intradermally, about half an inch below where the tail starts. 3 weeks later, bovine type II collagen was emulsified with equal parts of incomplete Freund's adjuvant, and 100 μL was injected intradermally, at a slightly different location near the start of the tail. Mice were then monitored, and their paws were assigned clinical scores according to their severity of swelling and erythema. 4 represents maximal redness and swelling, while 0 represents an absence. After the mice's paws had reached an average score of 10 (out of a possible 16), the mice were grouped, and treated as described below.

Near Infrared Imaging of ND-ODA-Cy5.5 and ND-ODA-Cy5.5-Dex

To determine if systemic delivery of ND-ODA and ND-ODA-Dex was feasible, free Cy5.5, ND-ODA-Cy5.5, and ND-ODA-Cy5.5-Dex were injected intravenously into the tail veins of separate mice (n=3 mice per treatment). Prior to injection, ND-ODA-Cy5.5 and ND-ODA-Cy5.5-Dex were bath sonicated for 1 min and filtered using a 10 μm cell strainer. Over the course of 24 h, the biodistribution of the treatments in the mice were tracked in real-time using near-infrared (NIR) imaging. After 24 h, the arthritic forelimbs and hindlimbs as well as major organs (liver, lungs, heart, kidney, brain, and spleen) were harvested and imaged again using NIR imaging. The results of this study informed the decision to perform local delivery in future studies.

Treatment of Mice with ND-ODA, ND-ODA-Dex, and Dex

Mice that had developed arthritis were treated with ND-ODA, ND-ODA-Dex, or Dex (n=4-6 mice per treatment). 2-3 limbs on each mouse were identified as injection sites. Forelimbs were injected at the wrists with 5 µL of 15 or 50 µg/mL ND-ODA (referred to as low and high ND-ODA, respectively), ND-ODA-Dex (0.1 µg/mL Dex and 15 µg/mL ND-ODA), or 0.1 µg/mL Dex. Hindlimbs were injected at both the ankles and knees with 5 µL at each site. Injections were performed using a Hamilton syringe, and the needle was guided directly to the joint spaces at the wrists, ankles, and knees. The mice were treated twice: once at day 5 and once at day 8 following the booster injection of collagen II. Mice used as controls did not receive any injections. The arthritic scores were monitored over the course of 14 days. The data are presented as mean total arthritic score±standard deviation (SD). To discern the therapeutic effects at each timepoint between the experimental groups, a two-way ANOVA with Tukey's post-hoc multiple comparisons test was performed. The final average scores for the individual paws for the forelimbs and hindlimbs were also compared. To discern differences between experimental groups, a one-way ANOVA with Tukey's post-hoc multiple comparisons test was performed. $p<0.05$ was considered significant.

After, mice were sacrificed, and their arthritic limbs were excised and stored in 4% paraformaldehyde. In order to proceed with x-ray micro-tomography (microCT) analysis, these samples were used directly. To proceed with histological and immunohistological analyses, the 4% paraformaldehyde was removed and the samples were rinsed in running water for 5 min. The samples were then transferred to glass containers, and decalcified for 24 h by submerging in CALCI-CLEAR™ decalcifier (NATIONAL DIAGNOSTICS®). Next, the samples were rinsed and stored in PBS. Paraffin-embedding and microtome sectioning were then performed. Samples were sectioned to a thickness of 4 µm.

Ex Vivo MicroCT Examination of Arthritic Mouse Limbs

The forelimbs and hindlimbs of a non-CIA mouse (n=4 limbs on 1 mouse), an untreated CIA mouse (n=4 limbs on 1 mouse), Dex-treated mice (n=3 limbs on 1 mouse), low ND-ODA-treated mice (n=8 limbs on 3 mice), high ND-ODA-treated (n=6 limbs on 2 mice), and ND-ODA-Dex-treated mice (n=6 limbs on 2 mice) were analyzed using microCT. 3D images of the arthritic forelimbs and hindlimbs were reconstructed and utilized to determine bone and total limb volumes. The bone volume (%) was calculated by dividing the bone volume by the total volume. Larger bone volume corresponds to less bone degradation. Bone volumes are represented as the average bone volume of all limbs or individual forelimb/hindlimb bone volume±standard deviation (SD). To discern differences between experimental groups, a one-way ANOVA with Tukey's post-hoc multiple comparisons test was performed. $p<0.05$ was considered significant.

Histological Examination

Hindlimb tissue sections were deparaffinized by soaking in two rinses of xylene, each for 10 min, and then rehydrated in a reverse ethanol series. To visualize cell infiltration, the samples were stained with Harris's hematoxylin and 1% alcoholic eosin Y. The stains were differentiated by soaking in 1% acid alcohol for 20 s in between the two staining steps. Images were visualized in bright field using an EVOS optical microscope.

Immunohistochemistry

Following deparaffinization and rehydration of hindlimb tissue sections, antigen retrieval was performed by immersing the tissue sections in 10 mM sodium citrate, and then heating to just below boiling for 20 min. The sections were then cooled and rinsed in running tap water. Next, endogenous peroxidases were blocked using the BLOXALL® solution in the IMMPRESS® EXCEL™ staining kit (VECTOR LABORATORIES®), followed by rinsing in a 10 mM sodium phosphate (pH=7.5, in 0.9% PBS) buffer solution. 2.5% horse serum in PBS was then added to the sections for 20 min to block non-specific binding. Polyclonal rabbit anti-mouse iNOS antibody (THERMOFISHER®, PA3-030A, dilution 1:50 in 2.5% horse serum) was added to the sections and incubated overnight at 4° C. Sections were washed twice in buffer solution for 5 min each, followed by the addition of the goat anti-rabbit IgG Amplifier Antibody (IMMPRESS EXCEL STAINING KIT®) for 15 min. Sections were then washed again in buffer solution for 5 min, and incubated with the horse antigoat IgG IMMPRESS EXCEL® Polymer Reagent for 30 min. Lastly, after 2 additional 5 min washes in buffer solution, the staining was visualized with 3,3'-diaminobenzidine (DAB) by mixing equal volumes of IMMPACT® DAB EqV Chromogen Reagent 1 and IMMPACT® Chromogen Buffer Reagent 2 and adding it directly to the samples. To ensure consistency between all samples, exactly 100 µL of DAB was added to each section for 5 min. In each batch of staining, a negative control was stained by adding PBS instead of the primary antibody. Images were visualized in bright field using an EVOS optical microscope.

Example 1

Adsorption Activity of DEX onto ND-ODA

The experimental results for ND-COOH (FIG. 2A) and ND-ODA (FIG. 2B) were in good agreement with both the Langmuir and Freundlich isotherm models, as determined by the Pearson's correlation coefficients. While it is not possible to draw any definitive conclusions about the adsorption mechanisms, this information may be used to compare the predicted adsorption properties between ND-COOH and ND-ODA. Since empirical Freundlich's fit parameters do not reveal any information about the adsorption mechanism, the Langmuir fit parameters for adsorption and bond strength (Amax and KL respectively) were used to compare the adsorption properties of ND-COOH and ND-ODA. In comparing the predicted strength of binding (KL) for the Langmuir model (Table 1, below), it is clear that Dex has markedly stronger adsorption to ND-ODA compared to ND-COOH. Conversely, ND-COOH has a much higher theoretical monolayer adsorption capacity than ND-ODA. However, it is important to note that this theoretical monolayer adsorption capacity cannot be realized in this system because of the limited solubility of Dex.

TABLE 1

Langmuir and Freundlich isotherm fit parameters.

| ND type | Langmuir Isotherm | | | Freundlich Isotherm | | |
|---------|-------------------|---|---|---------------------|---|---|
|         | Amax (mg/g) | $K_L$ (mL/g) | R | $K_f$ | n | R |
| ND-COOH | 1232.6 | 0.1 | 0.95 | 64.5 | 0.83 | 0.96 |
| ND-ODA  | 75.1 | 9.0 | 0.96 | 282.4 | 0.83 | 0.96 |

Example 2

FTIR of ND and ND-DEX

In comparing the FTIR spectra for ND-COOH and ND-ODA, the reduction of O-H bonds (~3400 cm$^{-1}$) and the disappearance of C=O bonds (1700 cm$^{-1}$) in addition to the rise of amide I (1650 cm$^{-1}$), amide II (1550 cm$^{-1}$), and C—H (~2800-3000 cm$^{-1}$) bonds on ND-ODA indicate that octadecylamine successfully replaced the —COOH groups on ND-COOH (FIG. 2C). FTIR analysis of ND-ODA-Dex showed that Dex was successfully adsorbed onto ND-ODA because of the appearance of C=O unconjugated ketone bonds (~1700 cm$^{-1}$), strengthening of C—H bonds (~2800-3000 cm$^{-1}$), and the narrowing of the —OH stretch (~3400 cm$^{-1}$) (FIG. 2C).

Example 3

Particle Size of ND-ODA and ND-DEX

Although the combined use of bath sonication and the 10 μm cell strainer removed large aggregates, particle size analysis of ND-ODA post-treatment revealed a multi-modal distribution of aggregates up to 7 μm in diameter, with the largest population centered around 1 μm (FIG. 2D). However, Dex adsorption seemed to break apart the larger (>3 μm) aggregates, instead forming a prominent, broad population centered around 1-2 μm. Additionally, both materials showed the presence of a smaller population centered around 150 nm.

Example 4

Effects of DEX on Macrophage Gene Expression

In keeping with its known anti-inflammatory effects, Dex treatment resulted in the significant dose-dependent reduction of pro-inflammatory M1-associated genes, including TNF, IL1B, and CCR7, especially in M1 macrophages (FIG. 3). Dex also decreased expression of M2a markers TIMP3, CCL22, and MRC1, which was also most pronounced in M1 macrophages. Dex treatment also caused the upregulation of M2c-associated CD163 and MERTK, which are both receptors involved in phagocytosis, in all three phenotypes, although these effects were not dose-dependent. Dex treatment did not significantly affect expression of non-phagocytosis-related M2c markers MMP7, MMP8, and VCAN, with the exception of small yet significant decreases in MMP7 expression by M1 macrophages. Finally, with respect to the potent angiogenic factors VEGFA, PDGFBB, and MMP9, the high dose of Dex decreased expression, especially by M1 macrophages.

Example 5

Effects of ND-ODA on Macrophage Gene Expression

Interestingly, treatment with ND-ODA caused significant dose-dependent downregulation of the genes encoding pro-inflammatory cytokines TNF and IL1B in both M0 and M1 macrophages (FIG. 4). ND-ODA also significantly reduced expression of M2a-associated TIMP3 in all three macrophage phenotypes. The highest dose of ND-ODA significantly reduced expression of the other M2a markers MRC1 and CCL22, especially in M1 macrophages. In contrast, ND-ODA treatment resulted in increased M2c-associated CD163 expression, with the effect most pronounced in M1 macrophages. Furthermore, high ND-ODA caused a significant downregulation of M2c markers MMP7 and VCAN in M1 macrophages. The high dose of ND-ODA also caused a significant reduction in angiogenic factors VEGFA in M1 macrophages, as well as PDGFB and MMP9 in both M1 and M2a macrophages.

Example 6

Effect of ND-ODA-DEX on Macrophage Gene Expression

The effect of ND-ODA-Dex on macrophage gene expression was compared to the sum of its parts: the low dose of Dex and the low dose of ND-ODA (FIG. 5). Compared to low Dex and low ND-ODA, ND-ODA-Dex significantly reduced TNF expression in M0 macrophages. The addition of DEX to ND-ODA also increased the effect of ND-ODA on downregulation of TNF expression in M1 macrophages. The combination of Dex and ND-ODA did not significantly affect the ability of either individual component to reduce IL1B expression, but ND-ODA-Dex did significantly reduce CCR7 expression compared to low ND-ODA in M1 macrophages. Compared to both low Dex and low ND-ODA, ND-ODA-Dex also significantly reduced expression of the M2a markers TIMP3 and CCL22. While downregulation of TIMP3 was only significant in M0 and M2a macrophages, downregulation of CCL22 was significant in all three phenotypes. Surprisingly, unlike its components, ND-ODA-Dex did not increase expression of the M2c-associated phagocytic markers CD163 or MERTK in any macrophage phenotype compared to M0 controls. However, ND-ODA-Dex did significantly decrease expression of the M2c marker MMP7 in M1 macrophages and of the angiogenic factors VEGFA, PDGFB, and MMP9 in both M0 and M1 macrophages compared to both low Dex and low ND-ODA.

Example 7

Figure 6A:
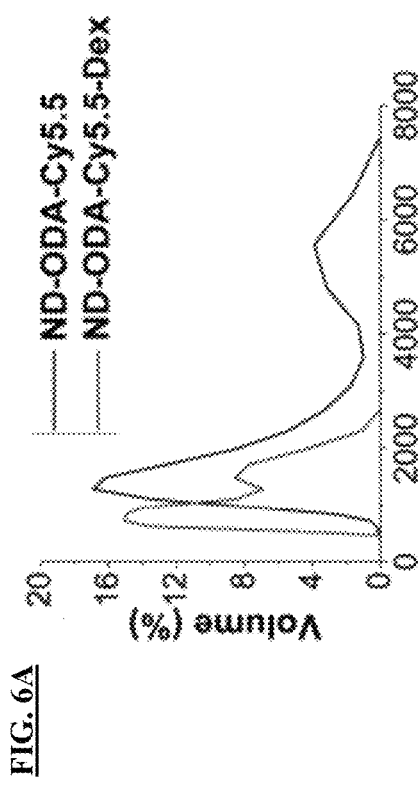
FIG. 6A depicts a particle size analysis of ND-ODA-Cy5.5 and ND-ODA-Cy5.5-Dex.
Figure 6B:
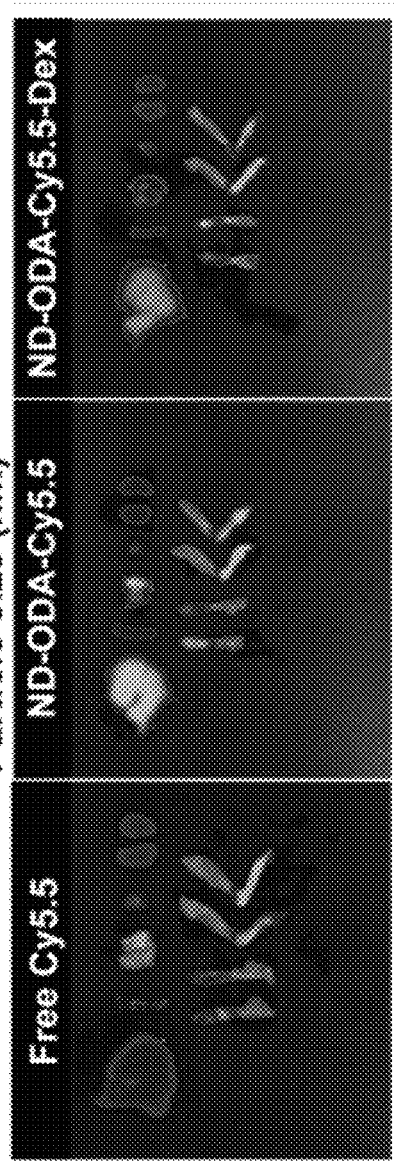
FIG. 6B depicts representative normalized ex vivo fluorescent images of harvested organs after 24 h (top: liver, spleen, lungs, heart, kidneys; bottom: forelimbs, hind limbs).

In Vivo Effects of Dexamethasone-Loaded Nanodiamond on a Mouse Model of Rheumatoid Arthritis ND-ODA-Cy5.5 complexes had a bimodal size distribution, with broad aggregate size peaks at ~1.5 μm and broad 5.5 which extended to ~7 μm (FIG. 6A). However, just as was seen with the non-Cy5.5-complexed ND (FIG. 2D), Dex adsorption appears to break up aggregate size, resulting in ND-ODA-Cy5.5-Dex aggregates that were centered around ~900 nm and 1.5 Ex vivo analysis of the biodistribution of free Cy5.5, ND-ODA-Cy5.5, and ND-ODA-Cy5.5-Dex suggests that targeting of the arthritic limbs was achieved within 24 h (FIG. 6B). When comparing ND-ODA-Cy5.5 and ND-ODA-Cy5.5-Dex, a decrease in liver uptake can be seen for ND-ODA-Cy5.5-Dex. This may be due to the size difference, since smaller particle sizes often result in the ability to avoid uptake by macrophages of the RES. Interestingly, the free Cy5.5 dye selectively accumulated in the arthritic joints within 24 h. Although, it has been suggested that if the study were longer, the Cy5.5 conjugated to the ND platforms would be more stable and fluoresce longer compared to the free dye.

While ND-ODA-Cy5.5 and ND-ODA-Cy5.5-Dex have shown the ability to passively target the arthritic limbs, their systemic delivery still resulted in significant accumulation in other organs, particularly the liver. These results informed the decision to use local delivery when administering ND-ODA and ND-ODA-Dex in order to ensure the therapeutic effects at the arthritic joints would be maximized.

Example 8

Therapeutic Efficacy of ND-ODA and ND-ODA-Dex

Figure 7A:
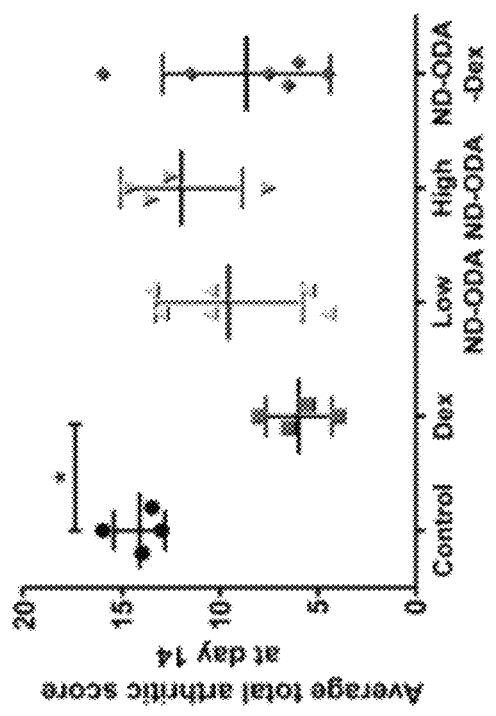
FIG. 7A depicts average total arthritic score for all 4 limbs over the course of 14 days following the first therapeutic injection. N=4-6.
Figure 7B:
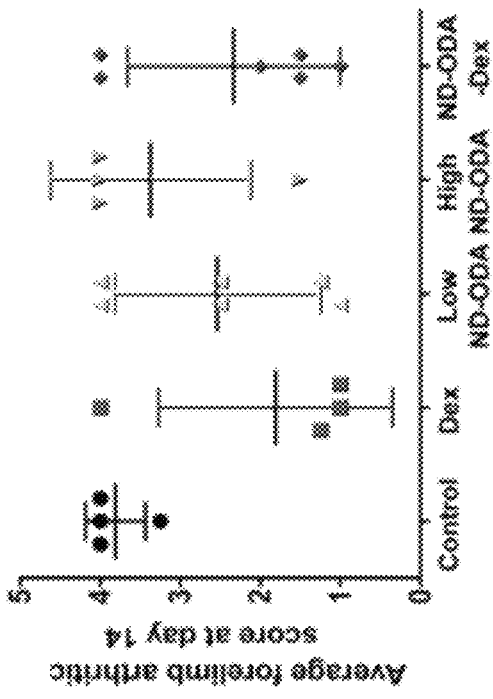
FIG. 7B depicts average total arthritic score of all 4 limbs.
Figure 7C:
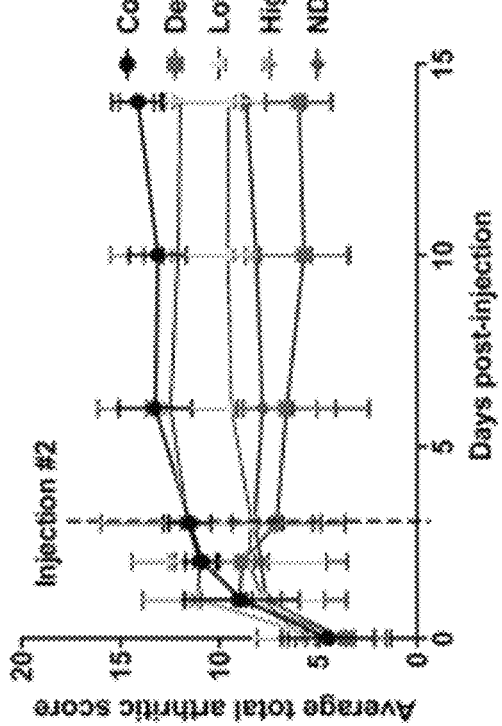
FIG. 7C depicts the score for individual hind limbs only for the same dataset.
Figure 7D:
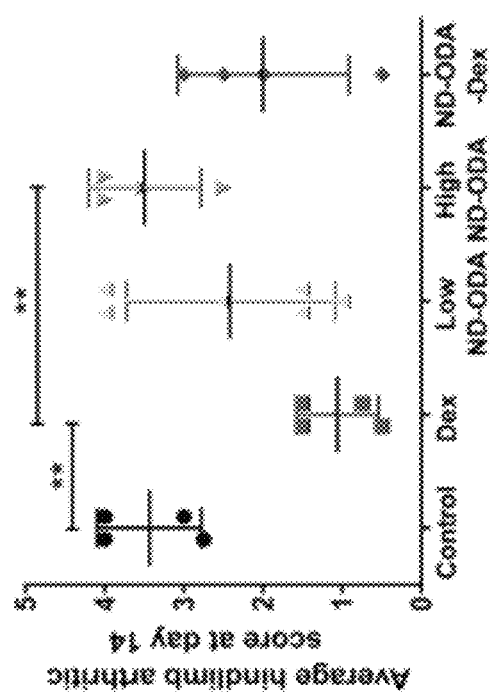
FIG. 7D depicts individual forelimbs only at the end of 14 days. For all of FIGS. 7A-7D, data are presented as mean±SD. $*p<0.05$, $**p<0.01$.
Figures 10A, 10B:
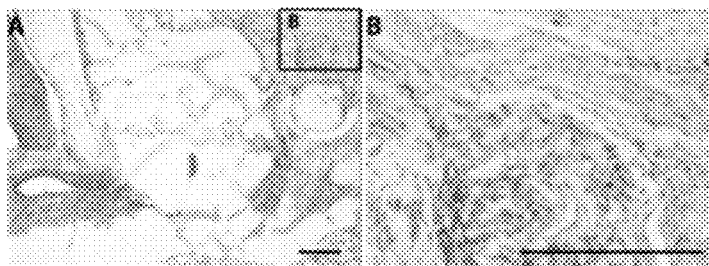
FIGS. 10A-10J depict immunohistological staining for hindlimbs of CIA mice that were untreated (FIGS. 10A and 10B), or treated with Dex (FIGS. 10C and 10D), low ND-ODA (FIGS. 10E and 10F), high ND-ODA (FIGS. 10G and 10H), or ND-ODA-Dex (FIGS. 10I and 10J). Images on the right are enlarged images as defined by the boxed sections on the right. The arthritic scores associated with each presented hindlimb tissue section are also displayed. All scale bars are 250 μm.
Figures 10C, 10D:
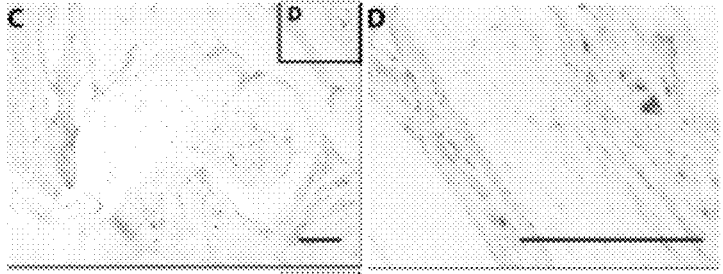
Figures 10E, 10F:
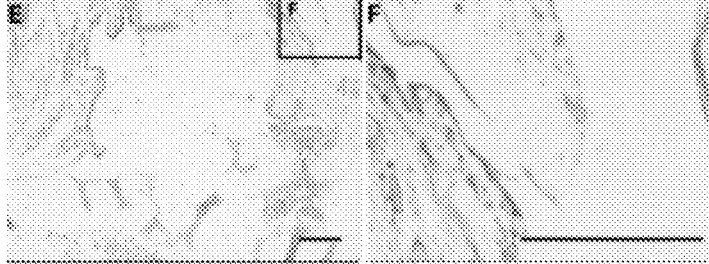
Figures 10G, 10H:
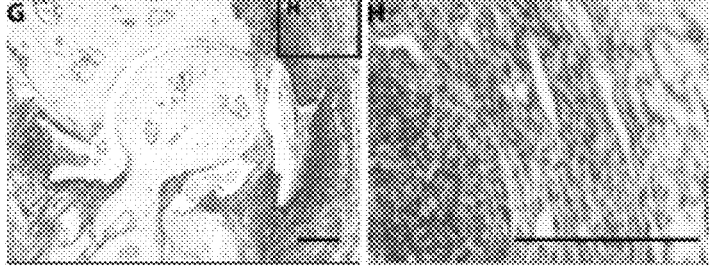
Figures 10I, 10J:
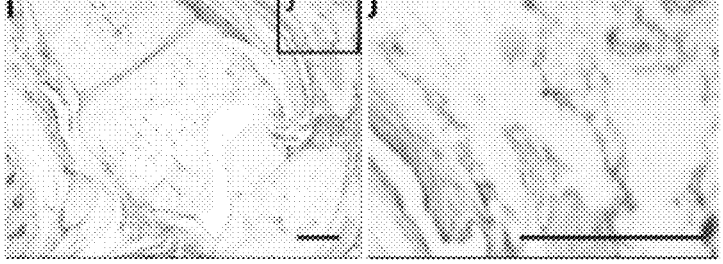

While the arthritic score continued to increase after the first therapeutic injection, the second therapeutic injection had a distinct effect on several groups (FIG. 7A). Following day 3, the arthritic scores of Dex-treated mice began to decrease, and the scores of low ND-ODA- and ND-ODA-Dex-treated mice leveled out. Meanwhile, the scores in the control and high ND-ODA treated mice continued to increase towards the maximum value of 16. At the end of study, only Dex-treated mice had shown significantly reduced arthritic scores compared to the control (FIG. 7B). However, a slight ND-ODA- and ND-ODA-Dex-treated groups also seem to show a slight, although insignificant decrease. Since the hindlimbs and forelimbs received separate treatments, the individual scores of the forelimb and hindlimb paws were also analyzed separately. The arthritic scores of the hindlimbs, which were treated with a total of 10 μL of therapeutics, were significantly decreased by Dex treatment compared to both the control and the high ND-ODA-treated mice, thus emphasizing the lack of a therapeutic effect at the higher ND-ODA concentration (FIG. 7C). Additionally, low ND-ODA- and ND-ODA-Dex-treated groups again appear to slightly decrease the arthritic scores, although the results are not significant due to the large scatter in the data. Interestingly, there were no significant differences between any of the groups when analyzing the arthritic scores of the forelimbs, which were only treated with 5 μL of therapeutics (FIG. 7D). This lack of a difference between groups is due to the fact that there is high scatter in all treatment groups, compared to the control.

These data suggest that both the low concentration of ND-ODA as well as ND-ODA-Dex may potentially have in vivo anti-inflammatory effects, although they require further investigation. Although the in vitro studies suggested that a higher dose of ND-ODA corresponds with stronger anti-inflammatory properties (FIG. 4), the data here do not support that this phenomenon translates in vivo. One reason for this discrepancy is that the higher dose of ND-ODA may be forming large aggregates upon introduction into the body, thus possibly avoiding phagocytosis by macrophages. At higher concentrations, ND particles/aggregates are more likely to be in contact with each other within the dispersion. Their contact may promote attractive interactions between ND surface functionalities, thus leading to re-aggregation. In this case, it may be expected that increased ND concentration should correlate with increased opsonin adsorption, and, consequently, macrophage uptake. However, if the aggregate size is shifted outside of the optimal 1-3 μm range, phagocytic efficiency will be decreased. Furthermore, if the aggregate size is shifted above 10 μm, the aggregates will not be phagocytosed at all.

Example 9

Effect of ND-ODA and ND-ODA-Dex on Bone Degradation

In both reconstructed microCT images of CIA control and high ND-ODA-treated forepaws, the bone surface appeared to be rough and patchy, indicating bone loss (FIG. 8A). However, the bone appeared to be much smoother and well-connected as a result of Dex, low ND-ODA, and ND-ODA-Dex treatment. While these images look very different, no significant differences in bone volume were detected in any of the analyses, including when comparing the non-CIA and CIA controls. This phenomenon is likely due to the fact that some of the experimental groups had either large scatter, a small number of replicates, or only a single data point. However, when analyzing the average bone volume across all limbs, Dex treatment appeared to drastically increase bone volume, and ND-ODA-Dex treatment appeared to result in a slight increase (FIG. 8B). When analyzing only the hindlimbs, Dex appeared to have the same effect (FIG. 8C). Additionally, low ND-ODA and ND-ODA-Dex appeared to markedly increase bone volume, although the scatter in the data was fairly large. High ND-ODA didn't appear to have any effects. Finally, when analyzing the forelimbs, Dex, again, appeared to have drastically increased bone volume, although only one forelimb was analyzed (FIG. 8D). Both low and high ND-ODA did not appear to have an effect. Although the scatter in the data collected for ND-ODA-Dex was large, it appeared to slightly increase bone volume.

Despite some of the limitations of this analysis, these results correlate well with the arthritic scoring data, and support the same conclusion that low ND-ODA and ND-ODA-Dex have anti-inflammatory properties in vivo.

Example 10

Effect of ND-ODA and ND-ODA-Dex on Cell Infiltration

Despite the fact that the untreated CIA control had a relatively low arthritic score of 2 (out of 4), there were marked signs of cell infiltration at the joint site, as evidenced by the large amount of hematoxylin staining that identifies cell nuclei (FIG. 9A). Likewise, high ND-ODA treatment appeared to result in a large amount of cell infiltration compared to the other treatment groups, which correlated with its arthritic score of 3, indicating substantial inflammation (FIG. 9D). Although ND-ODA-Dex had the lowest arthritic score, Dex, low ND-ODA, and ND-ODA-Dex all showed similar cell infiltration profiles, all of which indicated that cell infiltration was decreased by the treatments (FIGS. 9B-9C, 9E).

As previously described, there are a number of different types of resident and infiltrating synovial cells that are present at the arthritic joints. Because of their role in perpetuating inflammation in rheumatoid arthritis, pro-inflammatory M1 macrophages are one of the most abundant cell types at the arthritic sites. Therefore, it is likely that a large fraction of the cells that are present in the CIA control and high ND-ODA-treated hindlimb joints are M1 macrophages, which, when treated with Dex, ND-ODA, or ND-ODA-Dex, exit the arthritic site. These data suggest that Dex, ND-ODA, and ND-ODA-Dex act upon macrophages to remove them and their pro-inflammatory activity from the arthritic joints.

Example 11

Effect of ND-ODA and ND-ODA-Dex on Inflammatory Expression iNOS levels correlated with the cell infiltration profiles, as the CIA control and high ND-ODA-treated hindlimbs had the most intense iNOS staining, as indicated by the darker brown color compared to the other treatment groups. These results provide stronger evidence that pro-inflammatory cells, such as M1 macrophages, are the most abundant cells at the arthritic site. Treatment with Dex, low ND-ODA, and ND-ODA-Dex reduces iNOS levels, indicating that the treatments were anti-inflammatory. When compared to Dex, both low ND-ODA and ND-ODA-Dex appeared to have slightly darker staining, although it was still much less than the CIA control and high ND-ODA treatment groups. These data suggest that low ND-ODA and ND-ODA-Dex both have anti-inflammatory effects on arthritic joints, although their efficacy is not as strong as seen in Dex.

CONCLUSIONS

In investigating the therapeutic effects of Dex, ND-ODA, and ND-ODA-Dex on CIA mice, it was discovered that ND-ODA, delivered at a low dose, and ND-ODA-Dex have slight anti-inflammatory effects at the arthritic joints when delivered locally, although the results were variable among animals. Interestingly, ND-ODA's anti-inflammatory effect seemed to be abrogated when a higher dose was administered. These findings were supported through analysis of physical inflammation symptoms, bone degradation, cell infiltration profiles, and inflammatory protein levels. Although these results are promising, they support the need to conduct a more in-depth investigation.

INCORPORATION BY REFERENCE

The disclosures of each and every patent, patent application, and publication cited herein are hereby incorporated herein by reference in their entirety.

EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing inflammation in a patient, comprising administering a composition comprising octadecylamine surface-functionalized nanodiamonds, wherein the surface functionalized nanodiamonds do not bind a substantial amount of a therapeutic agent, wherein the surface-functionalized nanodiamonds have a particle size of between about 1 to about 10 μm in diameter.

2. The method of claim 1 wherein the site of inflammation is a lesion or diabetic ulcer.

3. The method of claim 1, wherein the inflammation is caused by rheumatoid arthritis, Crohn's disease, asthma, inflammatory bowel disease, venous leg ulcers, diabetes, psoriasis or multiple sclerosis.

4. The method according to claim 1, wherein the composition is delivered to the skin, the intestine, the lungs, trachea, or kidney of the subject.

5. The method according to claim 1, wherein the patient's macrophages phagocytose the surface-functionalized nanodiamonds.

6. The method according to claim 1, wherein the surface-functionalized nanodiamonds have a particle size ranging from 1 μm to 7 μm.

7. The method according to claim 1, wherein the surface-functionalized nanodiamonds have a particle size of about 1 μm.

8. The method according to claim 1, wherein the surface-functionalized nanodiamonds are locally administered.

* * * * *